(12) United States Patent
Lee et al.

(10) Patent No.: US 12,431,229 B2
(45) Date of Patent: Sep. 30, 2025

(54) MEDICAMENT DELIVERY DEVICE WITH AN ADJUSTABLE AND PIECEWISE ANALYTE LEVEL COST COMPONENT TO ADDRESS PERSISTENT POSITIVE ANALYTE LEVEL EXCURSIONS

(71) Applicant: Insulet Corporation, Acton, MA (US)

(72) Inventors: Joon Bok Lee, Acton, MA (US); Eric Benjamin, Cambridge, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 406 days.

(21) Appl. No.: 17/691,829

(22) Filed: Mar. 10, 2022

(65) Prior Publication Data
US 2022/0293234 A1    Sep. 15, 2022

Related U.S. Application Data

(60) Provisional application No. 63/158,918, filed on Mar. 10, 2021.

(51) Int. Cl.
*G16H 20/13*    (2018.01)
*A61M 5/172*    (2006.01)

(52) U.S. Cl.
CPC .......... *G16H 20/13* (2018.01); *A61M 5/1723* (2013.01); *A61M 2205/52* (2013.01); *A61M 2230/201* (2013.01)

(58) Field of Classification Search
CPC . G16H 20/13; A61M 5/1723; A61M 2205/52; A61M 2230/201
See application file for complete search history.

(56) References Cited

U.S. PATENT DOCUMENTS

| 303,013 A | 8/1884 | Horton |
|---|---|---|
| 2,797,149 A | 6/1957 | Skeggs |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Steven G. S. Sanghera
(74) *Attorney, Agent, or Firm* — Goodwin Procter LLP

(57) ABSTRACT

The exemplary embodiments may modify a glucose cost component of the cost function of the control loop of an insulin delivery device to compensate for persistent positive low level glucose excursions relative to a target glucose level. The exemplary embodiments may enable use of different glucose cost component functions for different glucose levels of the user. These glucose cost component functions may be employed in piecewise fashion with a different piece being applied for each respective range of glucose level values for the user. The final glucose cost function for calculating the glucose cost component may be a weighted combination of a piecewise glucose cost function and a weighted standard cost function (such as a quadratic function). The weights may reflect the magnitude and/or persistence of glucose excursions relative to a target glucose level.

17 Claims, 10 Drawing Sheets

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kunstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |

(56) References Cited

U.S. PATENT DOCUMENTS

| | | |
|---|---|---|
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Ebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Ebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |

(56) References Cited

U.S. PATENT DOCUMENTS

| | | |
|---|---|---|
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Ebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |

(56) References Cited

U.S. PATENT DOCUMENTS

| | | |
|---|---|---|
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0037159 A1* | 2/2012 | Mulqueeny ......... A61M 16/026 128/204.23 |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0066831 A1* | 2/2019 | Mairs ..................... G16H 20/17 |
| 2019/0076600 A1 | 3/2019 | Grosman et al. |
| 2019/0175080 A1* | 6/2019 | Varsavsky .......... A61B 5/14865 |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0075151 A1* | 3/2020 | Long .................... A61N 5/1031 |
| 2020/0101222 A1 | 4/2020 | Intereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1* | 2/2021 | Hayter .................. G16H 10/60 |
| 2021/0098105 A1 | 4/2021 | Lee et al. |
| 2021/0138264 A1* | 5/2021 | Isola .................... A61N 5/103 |
| 2022/0023536 A1 | 1/2022 | Graham et al. |
| 2022/0375563 A1* | 11/2022 | Rackauckas ........... G16H 10/60 |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |

(56) References Cited

FOREIGN PATENT DOCUMENTS

| | | |
|---|---|---|
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 200032258 A1 | 6/2000 |
| WO | 0172354 A2 | 10/2001 |
| WO | 2002015954 A1 | 2/2002 |
| WO | 2002043866 A2 | 6/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 Vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

(56) References Cited

OTHER PUBLICATIONS

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech, vol. Diabetes Technology Society ;(5): 1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

(56) References Cited

OTHER PUBLICATIONS

International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16- line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on IOS 11", GoToTags, Sep. 11, 2017, web <https://gototags.com/blog/read-hfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

\* cited by examiner

MEDICAMENT DELIVERY DEVICE WITH AN ADJUSTABLE AND PIECEWISE ANALYTE LEVEL COST COMPONENT TO ADDRESS PERSISTENT POSITIVE ANALYTE LEVEL EXCURSIONS

RELATED APPLICATIONS

This application claims the benefit of U.S. Provisional Patent Application No. 63/158,918, filed Mar. 10, 2021, the contents of which are incorporated herein by reference in their entirety.

BACKGROUND

Some insulin pump systems may use a closed loop control system for regulating the amount of insulin delivered at fixed intervals, such as every 5 minutes. The closed loop algorithms used by the control system may employ a penalty for large insulin deliveries that is balanced in a cost function with a penalty for glucose level excursions. The use of the cost function typically results in smaller automated insulin deliveries that are delivered more frequently than with manually delivered boluses. The closed loop system may reassess a patient's need more often than a manual approach.

SUMMARY

In accordance with an inventive facet disclosed herein, a diabetic treatment medicament delivery device includes a non-transitory storage medium for storing computer programming instructions for controlling operation of the diabetic treatment medicament delivery device. The diabetic treatment medicament delivery device also includes a processor for executing the computer programming instructions to cause the processor to determine a selected basal diabetic treatment medicament dosage to be delivered by the diabetic treatment medicament delivery device to a user from among candidate basal diabetic treatment medicament dosages. The determining includes determining the selected basal diabetic treatment medicament dosage based upon costs of the candidate basal diabetic treatment medicament dosages. The cost is determined by a cost function for determining a cost for each of the candidate basal diabetic treatment medicament dosages, where, for each of the candidate basal diabetic treatment medicament dosages, the cost function includes a glucose cost component that punishes glucose excursions relative to a target glucose level that are anticipated to be experienced by the user if the candidate basal diabetic treatment medicament dosage is delivered to the user by the diabetic treatment medicament delivery device. The glucose cost component varies in accordance with a first distribution function when the anticipated glucose excursions to be experienced by the user are in a first range and varies in accordance with a second distribution function when the anticipated glucose excursions to be experienced by the user are in a second range that differs from the first range. The computer programming instructions also cause the processor to cause the determined basal diabetic treatment medicament dosage to be delivered from the diabetic treatment medicament delivery device to the user.

The glucose cost component may be a combination of a piecewise cost function and an additional cost function. The weights assigned to the piecewise cost function and the additional cost function in the glucose cost component may depend on the persistence and the magnitude of glucose excursions experienced by the user. The first distribution function may be a quadratic function. The second distribution function may be a linear function. The first distribution function may be an exponential function or a logarithmic function. The diabetic treatment medicament may include at least one of insulin, a glucagon-like peptide-1 (GLP-1) agonist, pramlintide, or a co-formulation of two of the foregoing. The cost function also may include a diabetic treatment medicament cost component that represents a penalty based on an amount of diabetic treatment medicament in each of the candidate basal diabetic treatment medicament dosages.

In accordance with another inventive facet disclosed herein, a medicament delivery device includes a non-transitory storage medium for storing computer programming instructions for controlling operation of the medicament delivery device. The device also includes a processor for executing the computer programming instructions as to cause the processor to determine a selected basal medicament dosage to be delivered by the medicament delivery device to a user from among candidate basal medicament dosages such that the determining the selected basal medicament dosage is based upon costs of the candidate basal medicament dosages. The cost is determined by a cost function for determining a cost for each of the candidate basal medicament dosages, where, for each of the candidate basal medicament dosages, the cost function includes an analyte level component that punishes analyte level excursions relative to a target analyte level that are anticipated to be experienced by the user if the candidate basal medicament dosage is delivered to the user by the medicament delivery device. The analyte cost component varies in accordance with a first distribution function when the anticipated analyte level excursions to be experienced by the user are in a first range and varies in accordance with a second distribution function when the anticipated analyte level excursions to be experienced by the user are in a second range that differs from the first range. The computer programming instructions also cause the processor to cause the determined basal medicament dosage to be delivered from the medicament delivery device to the user.

The analyte cost component may be a combination of a piecewise cost function and an additional cost function. The weights assigned to the piecewise cost function and the additional cost function in the analyte level cost component may depend on the persistence and the magnitude of analyte excursions experienced by the user. The first distribution function may be one of a quadratic function, an exponential function, a linear function, or a logarithmic function. The cost function also may include a medicament cost component that represents a penalty based on an amount of medicament in each of the candidate basal diabetic treatment medicament dosages.

In accordance with an additional inventive facet disclosed herein, a method is performed by a processor for controlling basal medicament deliveries by a medicament delivery device. The method includes, with the processor, determining a medicament cost for a candidate basal medicament dosage for delivery to a user by the medicament delivery device and determining an analyte level cost for the candidate basal dosage. The analyte level cost includes a piecewise cost function that uses a first function to calculate analyte level cost for a first range of analyte level values, a second function to calculate analyte level cost for a second range of analyte level values, an additional cost function, a weight applied to the piecewise cost function, and a weight applied to the additional cost function. Per the method, a cost for the candidate basal medicament dosage is determined with the processor using the medicament cost and the analyte level cost, and based on the cost, a decision whether to deliver the candidate basal medicament dosage is made.

The medicament may be insulin. The method may include calculating the weight applied to the piecewise function from historical glucose levels. Calculating the weight applied to the piecewise function may entail calculating an offset value that captures how often there are positive glucose excursions and how often the positive glucose excursions occur in the historical glucose levels. The weight applied to the additional function may be (1—the offset value). The piecewise function may be a combination of a quadratic function and a linear function.

DETAILED DESCRIPTION

Figure 1:
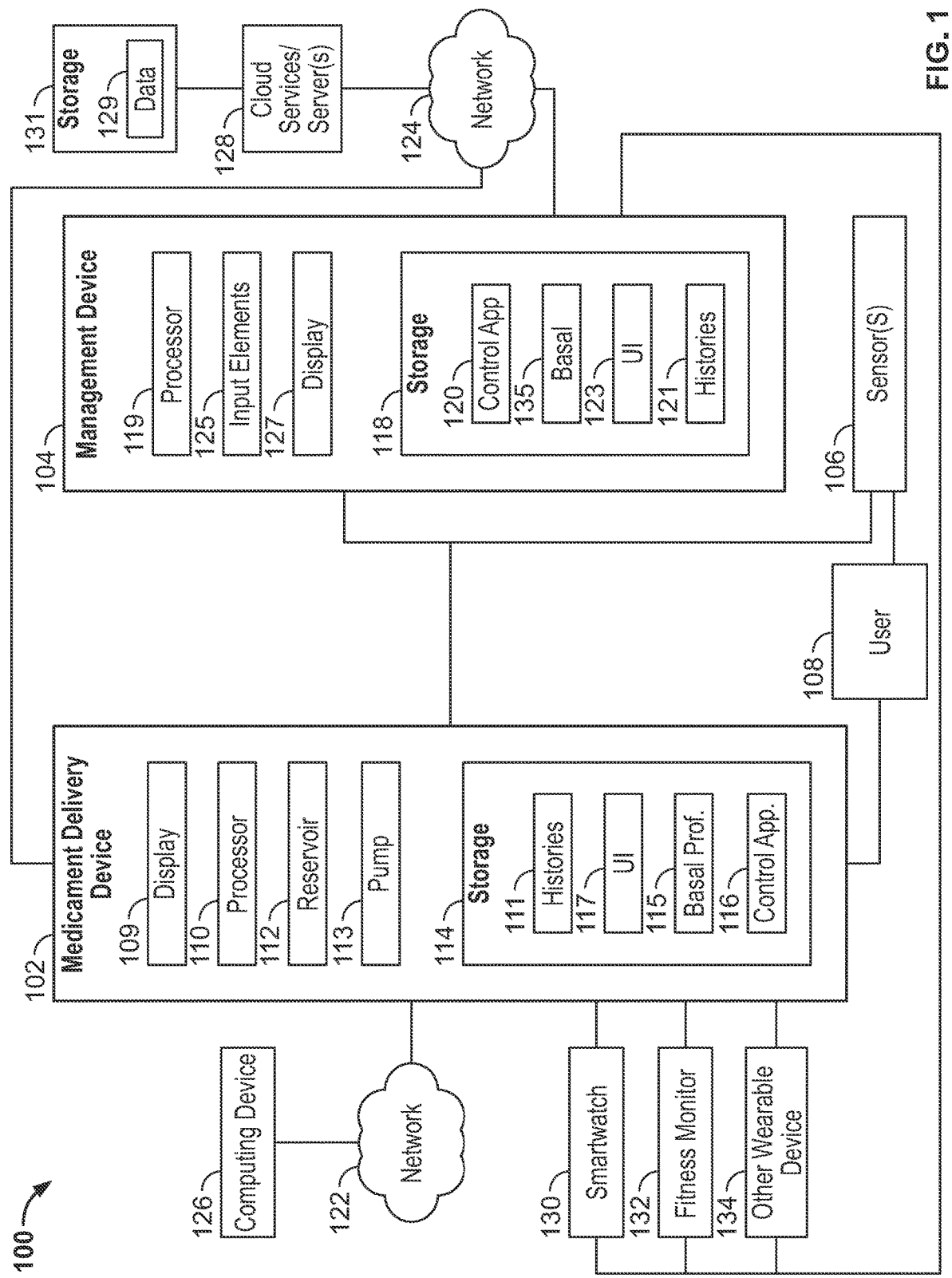
FIG. 1 an illustrative medicament delivery system suitable for the exemplary embodiments.

One problem suffered by many conventional insulin delivery devices is that low level glucose excursions above a target glucose level ("positive low level glucose excursions") are persistent. The control algorithm used by the control system does not readily remove such positive low level glucose excursions. The positive low level glucose excursions may persist for long periods. Such persistent positive low level glucose excursions are not desirable and may have a negative effect on a user's health. The persistent positive low level glucose excursions are a product of how a cost function for a control loop of the insulin delivery device is formulated. The control loop seeks to deliver insulin dosages that minimize cost. The cost function conventionally is configured to be conservative and is not aggressive as to such persistent positive low level glucose excursions.

The exemplary embodiments may modify a glucose cost component of the cost function of the control loop of an insulin delivery device to compensate for persistent positive low level glucose excursions relative to a target glucose level. The exemplary embodiments may apply different functions for the glucose cost component depending on the current reading of glucose level of the user. For example, a linear glucose cost component function rather than a quadratic glucose cost component may be employed closer to the glucose level target for the user. The linear glucose cost component function more aggressively punishes positive low level glucose excursions than a quadratic glucose cost component function. The quadratic glucose cost component function is better suited for punishing more significant positive glucose excursions relative to the glucose level target for the user.

The exemplary embodiments may enable use of different glucose cost component functions for different glucose levels of the user. These glucose cost component functions may be employed in piecewise fashion with a different piece being applied for each respective range of glucose level values for the user. Thus, an aggregate glucose cost component for a user may include separate glucose cost component functions that are each applied only if the glucose level of the user is in the range associated with the respective glucose cost component function. The glucose cost component functions may be, for example, linear functions, quadratic functions, exponential functions, logarithmic functions, etc.

The final glucose cost function for calculating the glucose cost component may be a weighted combination of a piecewise glucose cost function and a weighted standard cost function (such as a quadratic function). The weights may reflect the magnitude and/or persistence of glucose excursions relative to a target glucose level. The persistence and/or magnitude of the positive excursions are captured in an offset value. The offset value then may be used to calculate the weights of the cost functions. The piecewise function helps to more aggressively reduce positive low-level glucose excursions than how aggressively a standard single type of cost function reduces the low-level glucose excursions. The piecewise cost function is more heavily weighted when the glucose excursions are more persistent and of greater magnitude. Thus, the weights dynamically adjust the balance between the piecewise cost function and the standard cost function based on the glucose excursion history.

The exemplary embodiments are not limited to insulin delivery devices but more broadly encompass medicament delivery devices that seek to keep an analyte level of a user at a target level. As will be elaborated upon below, the medicament is not limited to insulin but rather may be any of a wide variety of medicaments. Further, the analyte level need not be a glucose level of a user. Other analyte levels such as heart rate, body temperature, blood pressure, hormonal levels, respiration rate, etc. may be measured and used by the control loop. Examples of insulin delivery devices will be detailed below but are intended to be illustrative and not limiting.

FIG. 1 depicts an illustrative medicament delivery system 100 that is suitable for delivering a medicament to a user 108 in accordance with the exemplary embodiments. The medicament delivery system 100 includes a medicament delivery device 102. The medicament delivery device 102 may be a wearable device that is worn on the body of the user 108 or carried by the user. The medicament delivery device 102 may be directly coupled to a user (e.g., directly attached to a body part and/or skin of the user 108 via an adhesive or the like) or carried by the user (e.g., on a belt or in a pocket) with the medicament delivery device 102 being connected to an infusion site where the medicament is injected using a needle and/or cannula. In a preferred embodiment, a surface of the medicament delivery device 102 may include an adhesive to facilitate attachment to the user 108.

The medicament delivery device 102 may include a processor 110. The processor 110 may be, for example, a microprocessor, a logic circuit, a field programmable gate array (FPGA), an application specific integrated circuit (ASIC) or a microcontroller. The processor 110 may maintain a date and time as well as other functions (e.g., calculations or the like). The processor 110 may be operable to execute a control application 116 encoded in computer programming instructions stored in the storage 114 that enables the processor 110 to direct operation of the medicament delivery device 102. The control application 116 may be a single program, multiple programs, modules, libraries, or the like. The control application may be responsible for implementing the control loop that provides feedback and adjustments to medicament dosages that are delivered to a user. The processor 110 also may execute computer programming instructions stored in the storage 114 for a user interface 117 that may include one or more display screens shown on display 109. The display 109 may display information to the user 108 and, in some instances, may receive input from the user 108, such as when the display 109 is a touchscreen.

The control application 116 may control delivery of a medicament to the user 108 per a control approach like that described herein. The storage 114 may hold histories 111 for a user, such as a history of basal deliveries, a history of bolus deliveries, and/or other histories, such as a meal event history, exercise event history, glucose level history and/or the like. These histories may be processed as will be described below to adjust basal medicament dosages to help reduce or eliminate persistent positive low level medicament excursions. The storage 114 also may include one or more basal profiles 115 that are used when the medicament delivery device is operating in open loop mode. In addition, the processor 110 may be operable to receive data or information. The storage 114 may include both primary memory and secondary memory. The storage 114 may include random access memory (RAM), read only memory (ROM), optical storage, magnetic storage, removable storage media, solid state storage or the like.

The medicament delivery device 102 may include one or more housings for housing its various components including a pump 113, a power source (not shown), and a reservoir 112 for storing a medicament for delivery to the user 108. A fluid path to the user 108 may be provided, and the medicament delivery device 102 may expel the medicament from the reservoir 112 to deliver the medicament to the user 108 using the pump 113 via the fluid path. The fluid path may, for example, include tubing coupling the medicament delivery device 102 to the user 108 (e.g., tubing coupling a cannula to the reservoir 112) and may include a conduit to a separate infusion site.

There may be one or more communications links with one or more devices physically separated from the medicament delivery device 102 including, for example, a management device 104 of the user and/or a caregiver of the user, a sensor 106, a smartwatch 130, a fitness monitor 132 and/or another variety of wearable device 134. The communication links may include any wired or wireless communication links operating according to any known communications protocol or standard, such as Bluetooth®, Wi-Fi, a near-field communication standard, a cellular standard, or any other wireless protocol.

The medicament delivery device 102 may interface with a network 122 via a wired or wireless communications link. The network 122 may include a local area network (LAN), a wide area network (WAN) or a combination therein. A computing device 126 may be interfaced with the network, and the computing device may communicate with the medicament delivery device 102.

The medicament delivery system 100 may include one or more sensor(s) 106 for sensing the levels of one or more analytes. The sensor(s) 106 may be coupled to the user 108 by, for example, adhesive or the like and may provide information or data on one or more medical conditions and/or physical attributes of the user 108. The sensor(s) 106 may be physically separate from the medicament delivery device 102 or may be an integrated component thereof.

The medicament delivery system 100 may or may not also include a management device 104. In some embodiments, no management device is not needed as the medicament delivery device 102 may manage itself. The management device 104 may be a special purpose device, such as a dedicated personal diabetes manager (PDM) device. The management device 104 may be a programmed general-purpose device, such as any portable electronic device including, for example, a dedicated controller, such as a processor, a micro-controller, or the like. The management device 104 may be used to program or adjust operation of the medicament delivery device 102 and/or the sensors 106. The management device 104 may be any portable electronic device including, for example, a dedicated device, a smartphone, a smartwatch or a tablet. In the depicted example, the management device 104 may include a processor 119 and a storage 118. The processor 119 may execute processes to manage a user's glucose levels and to control the delivery of the medicament to the user 108. The medicament delivery device 102 may provide data from the sensors 106 and other data to the management device 104. The data may be stored in the storage 118. The processor 119 may also be operable to execute programming code stored in the storage 118. For example, the storage 118 may be operable to store one or more control applications 120 for execution by the processor 119. The one or more control applications 120 may be responsible for controlling the medicament delivery device 102, such as by controlling the AID delivery of insulin to the user 108. The storage 118 may store the one or more control applications 120, histories 121 like those described above for the medicament delivery device 102, one or more basal profiles 135 and other data and/or programs.

A display 127, such as a touchscreen, may be provided for displaying information. The display 127 may display user interface (UI) 123. The display 127 also may be used to receive input, such as when it is a touchscreen. The management device 104 may further include input elements 125, such as a keyboard, button, knobs, or the like, for receiving input form the user 108.

The management device 104 may interface with a network 124, such as a LAN or WAN or combination of such networks via wired or wireless communication links. The management device 104 may communicate over network 124 with one or more servers or cloud services 128. Data, such as sensor values, may be sent, in some embodiments, for storage and processing from the medicament delivery device 102 directly to the cloud services/server(s) 128 or instead from the management device 104 to the cloud services/server(s) 128. The cloud services/server(s) 128 may provide output from the model 115 as needed to the management device 104 and/or medicament delivery device 102 during operation.

Other devices, like smartwatch 130, fitness monitor 132 and wearable device 134 may be part of the medicament delivery system 100. These devices 130, 132 and 134 may communicate with the medicament delivery device 102 and/or management device 104 to receive information and/or issue commands to the medicament delivery device 102. These devices 130, 132 and 134 may execute computer programming instructions to perform some of the control functions otherwise performed by processor 110 or processor 119, such as via control applications 116 and 120. These devices 130, 132 and 134 may include displays for displaying information. The displays may show a user interface for providing input by the user, such as to request a change or pause in dosage or to request, initiate, or confirm delivery of a bolus of a medicament, or for displaying output, such as a change in dosage (e.g., of a basal delivery amount) as determined by processor 110 or management device 104. These devices 130, 132 and 134 may also have wireless communication connections with the sensor 106 to directly receive analyte measurement data.

A wide variety of medicaments may be delivered by the medicament delivery device 102. The medicament may be insulin for treating diabetes. The medicament may be glucagon for raising a user's glucose level. The medicament may also be a glucagon-like peptide (GLP)-1 receptor agonists for lowering glucose or slowing gastric emptying, thereby delaying spikes in glucose after a meal. Alternatively, the medicament delivered by the medicament delivery device 102 may be one of a pain relief agent, a chemotherapy agent, an antibiotic, a blood thinning agent, a hormone, a blood pressure lowering agent, an antidepressant, an antipsychotic, a statin, an anticoagulant, an anticonvulsant, an antihistamine, an anti-inflammatory, a steroid, an immunosuppressive agent, an antianxiety agent, an antiviral agents, a nutritional supplement, a vitamin, or co-formulations of two or more of the above.

The functionality described below for the exemplary embodiments may be under the control of or performed by the control application 116 of the medicament delivery device 102 or the control application 120 of the management device 104. In some embodiments, the functionality may be under the control of or performed by the cloud services or servers 128, the computing device 126 or by the other enumerated devices, including smartwatch 130, fitness monitor 132 or another wearable device 134.

The medicament delivery device 102 may operate in an open loop mode and in a closed loop mode. In the open loop mode, the user 108 manually inputs the amount of medicament to be delivered (such as per hour) for segments of the day. The inputs may be stored in a basal profile 115, 135 for the user 108. In other embodiments, a basal profile may not be used. The control application 116, 120 uses the input information from the basal profile 115, 135 to control basal medicament deliveries in open loop mode. In contrast, in the closed loop mode, the control application 116, 120 determines the medicant delivery amount for the user 108 on an ongoing basis based on a feedback loop. For an insulin delivery device, the aim of the closed loop mode is to have the user's glucose level at a target glucose level. The basal dosages may be delivered at fixed regular intervals, designated as cycles, such as every five minutes.

Figure 2:
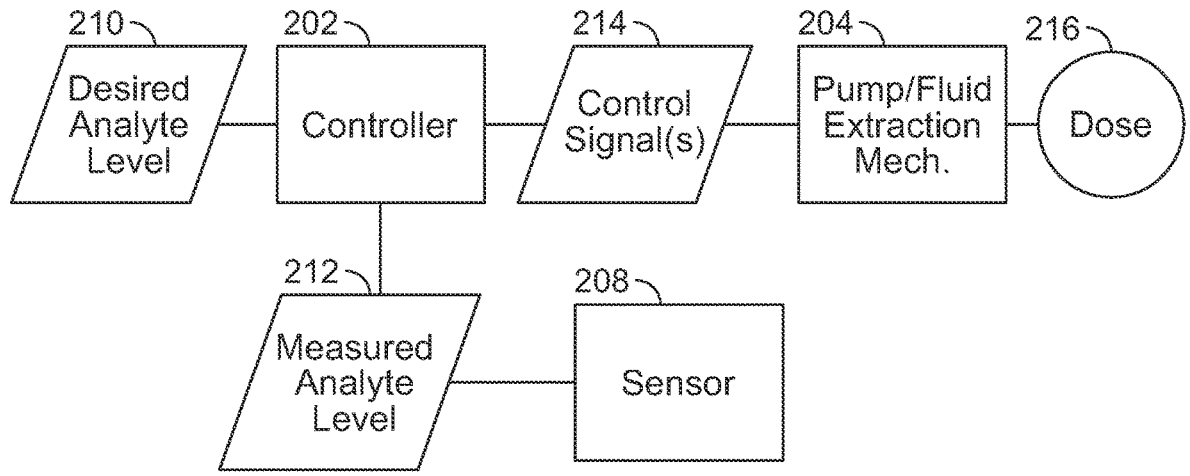
FIG. 2 depicts an illustrative control loop of exemplary embodiments for adjusting a medicament delivery dosage.

As was mentioned above, a control loop may be provided to adjust the basal delivery dosage based on current analyte level readings, such as glucose level readings, for example. FIG. 2 illustrates a simplified block diagram of an example of such a control loop 200 suitable for practicing an exemplary embodiment. The example control loop 200 may include a controller 202, a pump mechanism or other fluid extraction mechanism 204 (hereinafter "pump 204"), and a sensor 208. The controller 202, pump 204, and sensor 208 may be communicatively coupled to one another via a wired or wireless communication paths. The sensor 208 may be a glucose monitor in some exemplary embodiments, such as, for example, a continuous glucose monitor (CGM). The sensor 208 may, for example, be operable to measure glucose level values of a user to generate the measured analyte level 212.

As shown in the example, the controller 202 may receive a desired analyte level 210, indicating a desired analyte level or range for a user. The desired analyte level 210 may be received from a user interface to the controller 202 or other device or by an algorithm that automatically determines a desired analyte level 210 for a user. The sensor 208 may be coupled to the user and be operable to measure an approximate value of an actual analyte level of the user. For cases where the analyte level is a glucose level, it is worth noting that the measured glucose level is only an approximate value of a user's glucose level. There may be errors in the measured glucose levels. The errors may, for example, be attributable to factors, such as age of the sensor 208, location of the sensor 208 on a body of a user, environmental factors (e.g., altitude, humidity, barometric pressure), or the like. In response to the measured analyte level or value, the sensor 208 may generate a signal indicating the measured analyte level 212. The controller 202 may receive from the sensor 208 via a communication path the measured analyte level signal 212.

Based on the desired analyte level signal 210 and the measured analyte level signal 212, the controller 202 may generate one or more control signals 214 for directing operation of the pump 204. For example, one of the control signals 214 may cause the pump 204 to deliver a dose of medicament 216 to a user via output 206. The dose of medicament 216 may, for example, be determined based on a difference between the desired analyte level 210 and the actual analyte level 212. The cost function referenced above plays a role in determining the dosage as part of the closed loop control system as will be described below. The dose of medicament 216 may be determined as an appropriate amount of medicament to drive the actual analyte level of the user toward the desired glucose level. Based on operation of the pump 204 as determined by the control signals 214, the user may receive the dose of medicament 216 from the pump 204.

Figure 3:
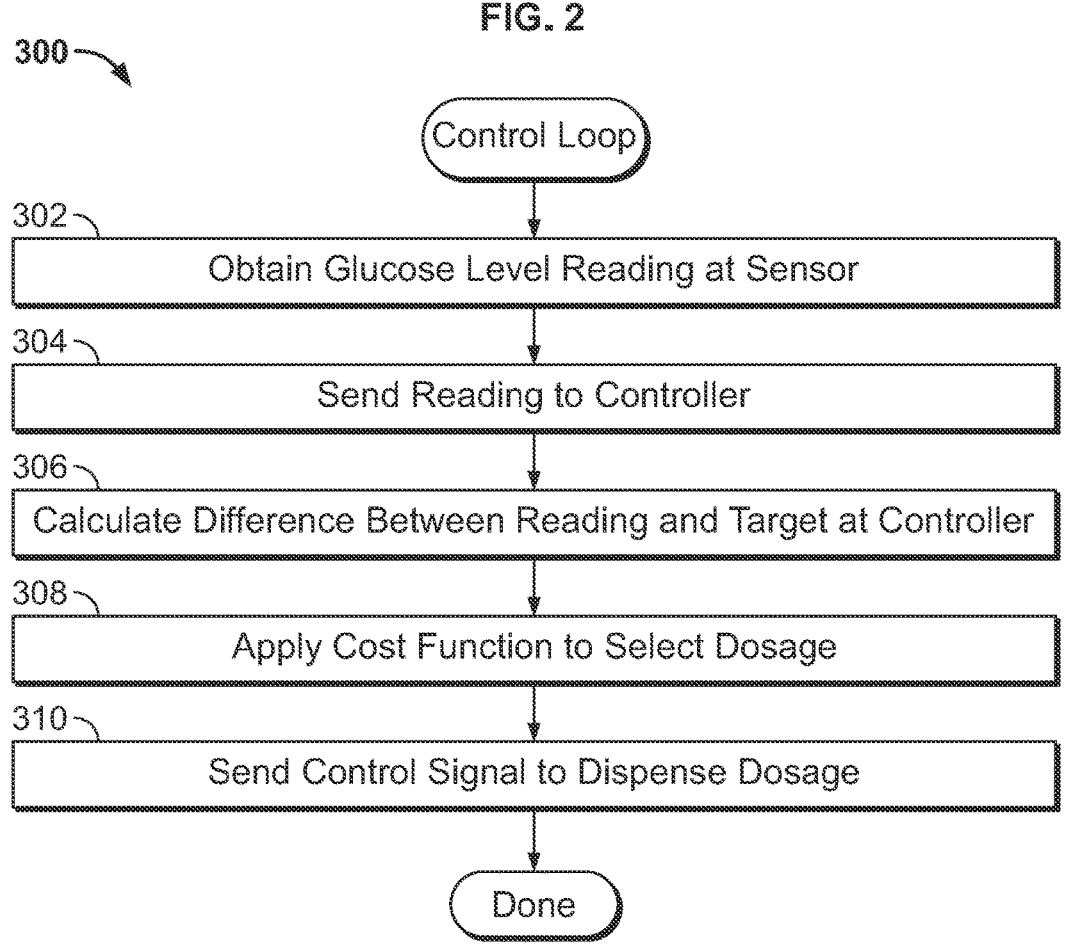
FIG. 3 depicts a flowchart of illustrative steps that may be performed in a control loop of exemplary embodiments.

FIG. 3 depicts a flowchart 300 of steps that may be performed by exemplary embodiments in determining what dose of medicament to deliver the user as part of the closed loop control system. These steps may be performed by controller 110, processor 119 or other components (at least in part), like smartwatch 130, fitness monitor or wearable device 134. That said, for purposes of simplicity below, the discussion just refers to controller 110. Initially, as was described above relative to FIG. 2, a glucose level reading is obtained by the sensor 208 at 302. The analyte level reading is sent via a signal 212 to the controller 202 at 304. The controller 202 calculates an error value as the difference between the measured analyte level 212 and the desired analyte level 210 at 306. The closed loop control system attempts to minimize the aggregate penalty of the cost function over a wide range of possible dosages. The cost function is applied to the possible dosages, and the dosage with the best cost function value is selected at 308. Depending on how the cost function is configured, the best value may be the lowest value or the highest value. The cost function used in exemplary embodiments will be described in more below. A control signal 214 may be generated by the controller 202 and sent to the pump 204 to cause the pump to deliver the desired medicament dose 216 to the user at 310.

As mentioned above, the medicament may be insulin and the analyte level sensed by the sensor(s) 106 may be glucose level. The cost function may be adjusted to address persistent low-level glucose level excursions for users. As a starting point for this discussion, it is helpful to review an exemplary cost function. An exemplary formulation for cost J is:

$$J = Q \cdot \sum_{i=1}^{M} G_p(i)^2 + R \cdot \sum_{i=1}^{n} I_p(i)^2$$

where Q and R are weight coefficients as mentioned above, $G_p(i)^2$ is the square of the deviation between the projected glucose level for an insulin dosage at cycle i and the projected glucose level for the basal insulin dosage, M is the number of cycles in the prediction horizon, $I_p(i)^2$ is the square of the deviation between the projected insulin delivered at cycle i and the insulin for basal insulin delivery, and n is the control horizon in cycles. Thus, $Q \cdot \Sigma_{i=1}^{M} G_p(i)^2$ is the weighted glucose cost, and $R \cdot \Sigma_{i=1}^{n} I_p(i)^2$ is the weighted insulin cost. The total cost J is the sum of the weighted glucose cost and the weighted insulin cost. A cycle has a fixed interval, such 5 minutes.

The exemplary embodiments may modify the glucose cost component of the cost function to compensate for low level glucose excursions relative to a target glucose level. More generally, the exemplary embodiments may apply different functions for the glucose cost component depending on the current reading of glucose level of the user. For example, a linear glucose cost component function rather than a quadratic glucose cost component may be employed closer to the glucose level target for the user. The linear glucose cost component function more aggressively punishes low level glucose excursions than a quadratic glucose cost component function does. The quadratic glucose cost component function is better suited for punishing more significant glucose excursions relative to the glucose level target for the user.

The exemplary embodiments may enable use of different glucose cost component functions for different glucose levels of the user. These glucose cost component functions may be employed in piecewise fashion with a different piece being applied for each respective range of glucose level values for the user. Thus, an aggerate glucose cost component for a user may be includes separate glucose cost component functions that are each applied only if the glucose level of the user is in the range associated with the respective glucose cost component functions. The functions may be, for example, linear functions, quadratic functions, exponential functions, logarithmic functions, etc.

Figure 4:
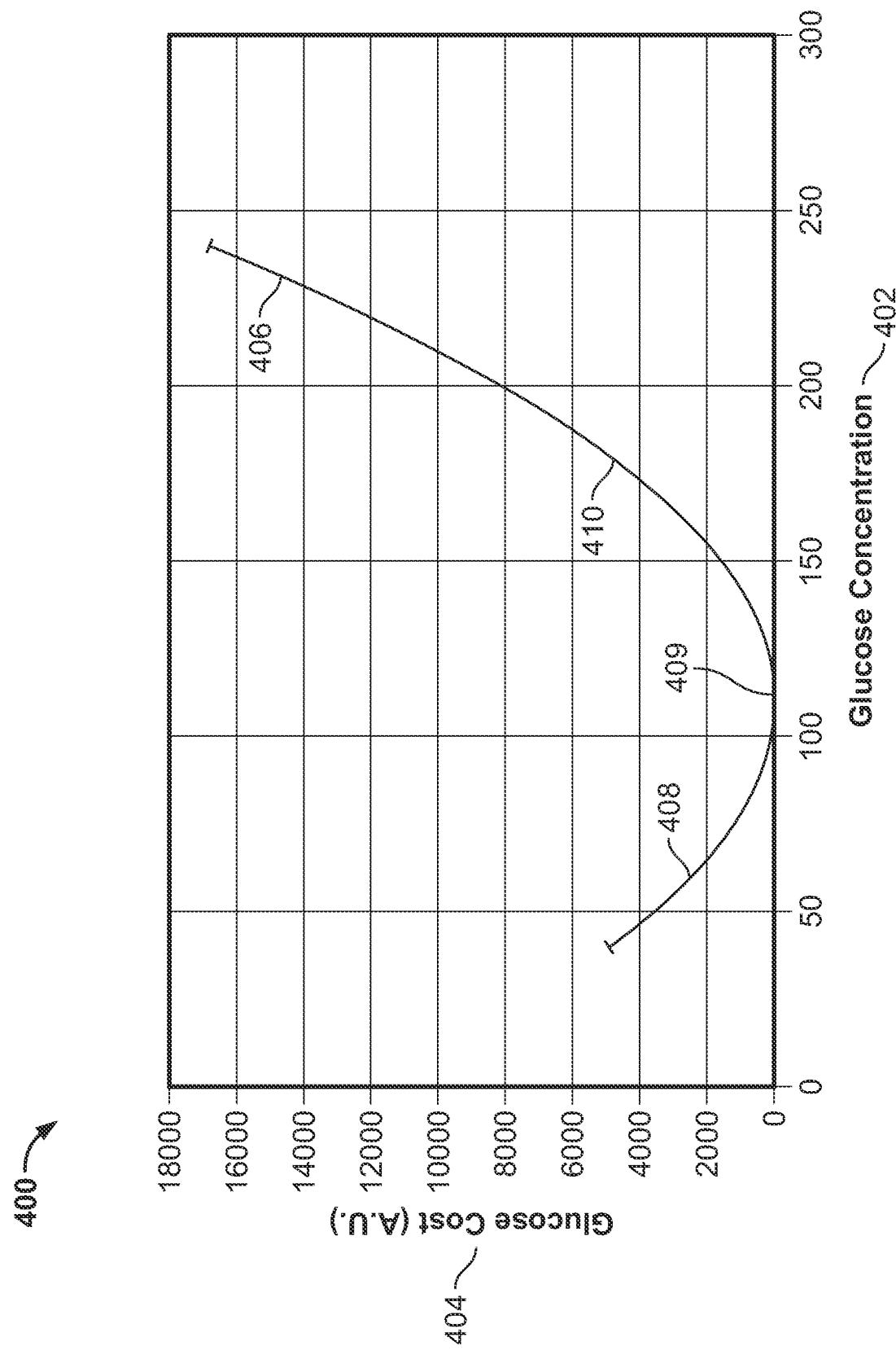
FIG. 4 depicts an illustrative quadratic glucose cost function.

FIG. 4 depicts a graph 400 of an illustrative quadratic glucose cost component that may be used in a control loop of an insulin delivery device. The graph plots a curve 406 of glucose concentration 402 of a user relative to glucose cost 404. The glucose concentration 402 is expressed as mg/dL and the glucose cost is expressed in arbitrary units (A.U.). The curve extends from a glucose concentration of approximately 40 mg/dL to approximately 240 mg/dL. It is presumed that the target glucose concentration 409 for the user is 110 mg/dL. Other target concentrations may be used. The desired range of glucose values is between the hypoglycemic threshold of 70 mg/dL and the hyperglycemic threshold of 180 mg/dL. The slope of curve 406 is negative when the user's glucose concentration is below the target glucose concentration 409 of 110 mg/dL. Thus, the glucose cost 404 drops until the target glucose concentration 409 is reached. In section 408 of the curve 406, the slope starts off greater and lessens as the target glucose concentration is reached. The result is that section 408 flattens out near the target glucose concentration 409. Hence, the quadratic function decreases insulin delivery more aggressively when glucose concentration is below the hypoglycemic threshold of 70 mg/dL, but is less aggressive in its reduction of insulin delivery as the target glucose concentration 409 is reached (going from left to right).

With the quadratic function curve 406 of FIG. 4, the slope of the curve reaches 0 at the target glucose concentration 409 and become positive thereafter. Thus, the slope of section 410 of the quadratic function curve 406 is positive. The positive curve indicates that the glucose cost increases as the glucose concentration increases. The slope of section 410 starts off modestly near the target glucose concentration 409 and increases. After 180 mg/dL, the slope becomes quite great to encourage more insulin delivery as the glucose cost is high. The helps to discourage the user from becoming hyperglycemic.

One drawback of using a quadratic glucose cost function like that shown in FIG. 4 is that it is difficult to get rid of positive low level glucose excursions. The glucose cost for such excursions is negligible as indicated by the flatness of the curve 406 immediately to the right and left of the target glucose concentration. Hence, the control loop using such a quadratic glucose cost function is not punished much for such positive low level glucose excursion and as a result, is not especially effective in eliminating them.

Figure 5:
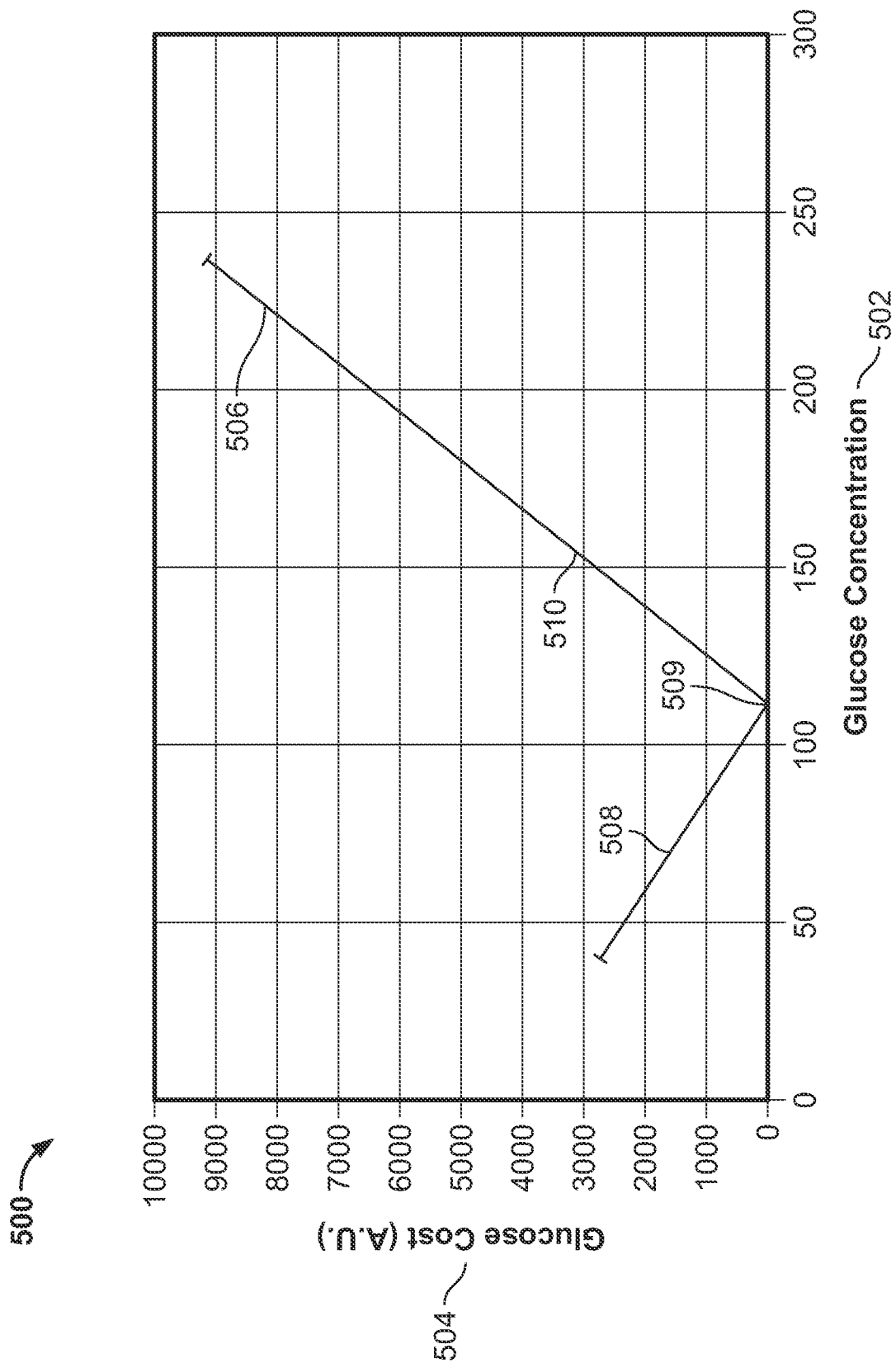
FIG. 5 depicts an illustrative linear glucose cost function.

FIG. 5 depicts a plot 500 of a curve 506 of linear glucose cost function showing glucose concentration 502 versus glucose cost. The curve 506 has a portion 508 with a negative slope extending between 40 mg/dL and the target glucose concentration 509 of 110 mg/dL. Thus, when the glucose concentration 502 is below the target glucose concentration 509, the glucose cost decreases until the target glucose concentration 509 is reached. As the glucose concentration 502 increases above the target glucose concentration 509 in portion 510 of the curve 506, the slope of the curve is positive and constant. This indicates that the glucose cost 504 increases linearly as the glucose concentration 502 increases above the target glucose concentration.

The exemplary embodiments may combine analyte level cost functions. For instance, a first analyte level cost function may be used for a first range of analyte levels and a second analyte cost function may be used for a second range of analyte levels. In other instances, more than two analyte level cost functions may be used. Such analyte level cost functions that combine multiple analyte level cost functions are referred to herein as "piecewise functions."

Figure 6:
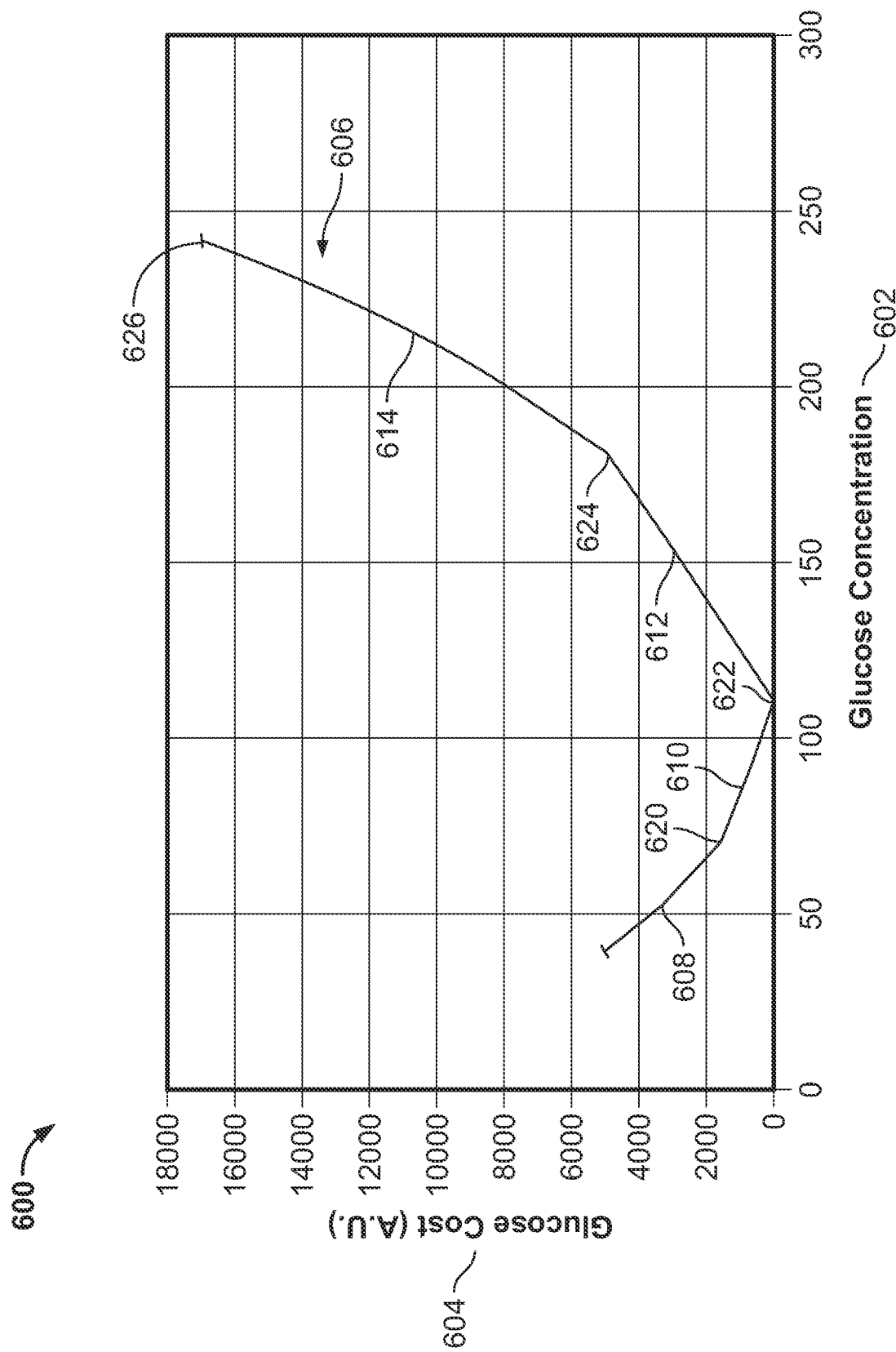
FIG. 6 depicts an illustrative piecewise glucose cost function that may be used in exemplary embodiments.

For an insulin delivery device, the exemplary embodiments may combine multiple glucose cost functions into a piecewise glucose cost function. FIG. 6 depicts an example of a piecewise glucose cost function wherein a linear cost function is combined with a quadratic cost function. FIG. 6 shows a graph 600 of the curve 606 of glucose concentration 602 relative to glucose cost 604 for the piecewise glucose cost function. In this piecewise glucose cost function, the quadratic function is used for values below the hypoglycemic threshold 620 of 70 mg/dL as indicated by portion 608 that extends from 40 mg/dL to 70 mg/dL. The quadratic cost function is also used for glucose concentration 602 values above the hyperglycemic threshold 624 of 180 mg/dL in portion 614 of the curve 606. The quadratic cost function is suitable for when the glucose concentration 602 of the user is below the hypoglycemic threshold 620 to increase the glucose cost 604 rapidly. The quadratic function also is suitable when the glucose concentration 602 of the user is above the hyperglycemic threshold 624 because it is desirable to increase the glucose cost 604 rapidly to discourage additional increases in glucose concentration 602.

A linear cost function is used for portion 610 of the curve 606 between the hypoglycemic threshold 620 and the target glucose concentration 622. The linear cost function increases the glucose cost more rapidly than the quadratic cost function in this portion 610. A linear cost function is used for the portion 612 of the curve 606 between the target glucose concentration 622 and the hyperglycemic threshold 624. The linear function increases the glucose cost 604 more rapidly than the quadratic glucose cost function for this range of glucose concentration values and thus more aggressively reduces low level positive glucose excursions.

Figure 7:
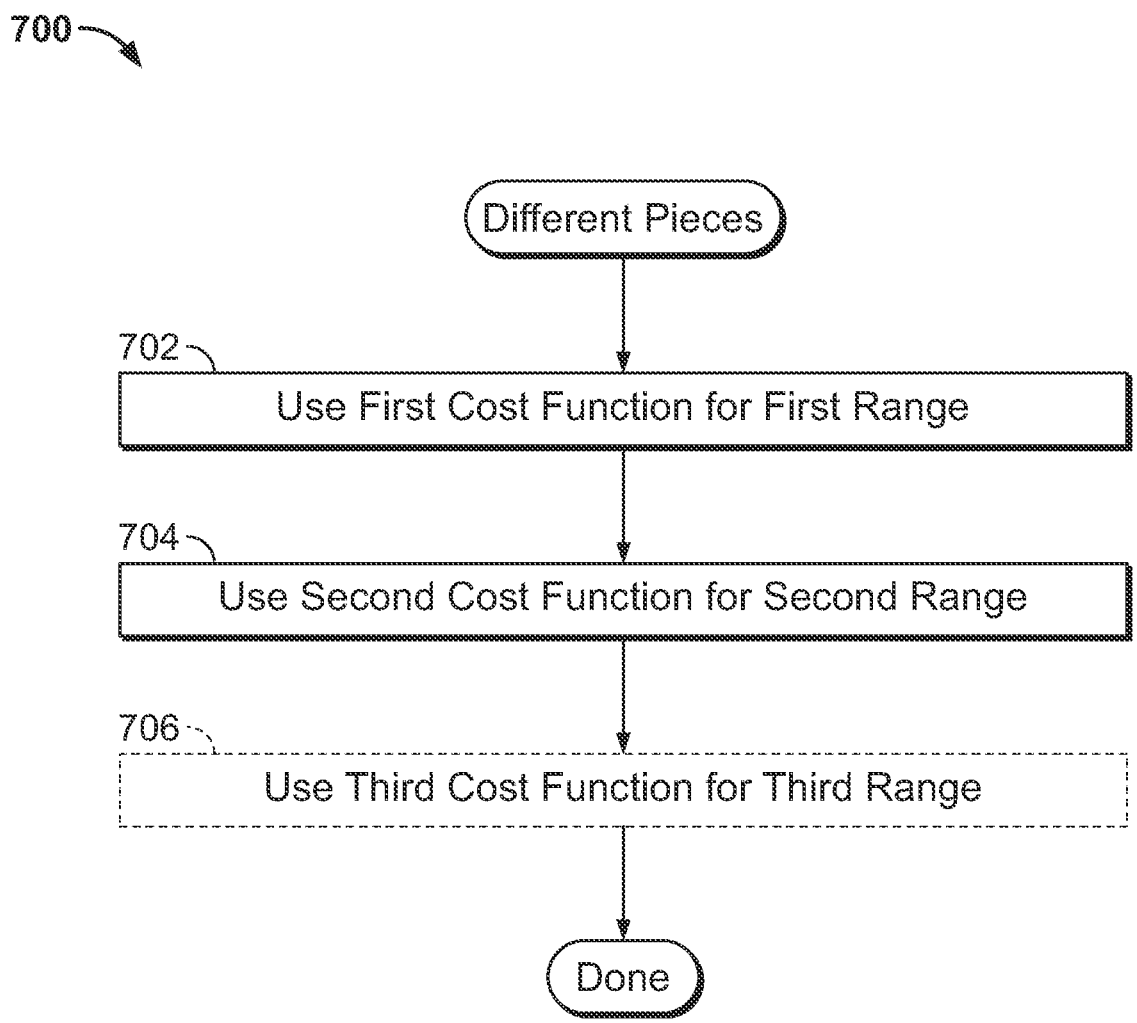
FIG. 7 depicts a flowchart of illustrative steps that may be performed in exemplary embodiments to use different functions in a piecewise cost function.

FIG. 7 depicts a flowchart 700 of illustrative steps that may be performed in exemplary embodiments to use a piecewise analyte level cost function. At 702, the piecewise cost function uses a first analyte level cost function (e.g., a linear glucose cost function) for a first range of analyte levels for a user. At 704, the piecewise cost function uses a second analyte level cost function (e.g., a quadratic glucose cost function) for a second range of analyte levels for the user. The piecewise analyte level cost function may use more than two cost functions to determine the costs of additional ranges of analyte levels. Any number of analyte level cost functions may be included in the piecewise analyte level cost function. At 706, an optional third analyte level cost function may be used for a third range of analyte levels. This step 706 is shown to illustrate that more than two analyte cost functions may be used in the piecewise analyte level cost function.

Figure 8:
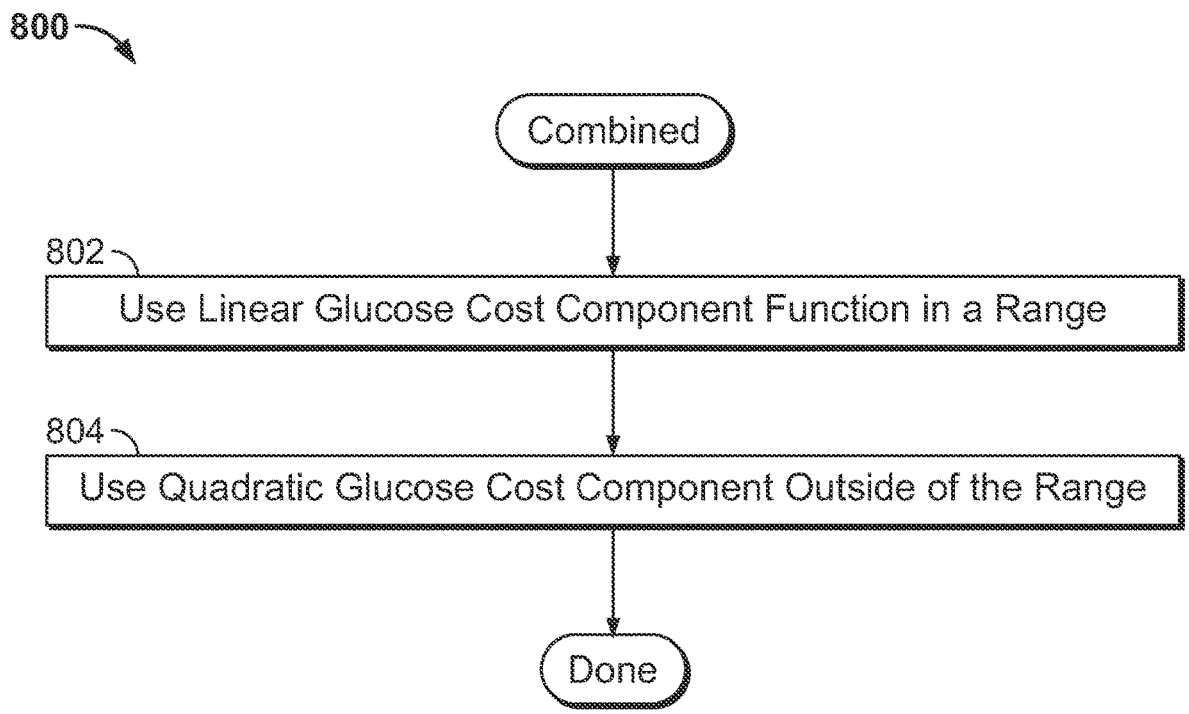
FIG. 8 depicts a flowchart of illustrative steps that may be performed in exemplary embodiments to combine a quadratic function and a linear function in a piecewise glucose cost function.

The use of such a piecewise analyte level function may be used by a medicament delivery device that delivers insulin to a user. In such a case, the glucose level of the user is the analyte level that is sensed and is used in the control loop. In the exemplary embodiments, a linear glucose cost function and a quadratic glucose cost component may be used as part of a piecewise glucose cost component. As shown in the flowchart 800 of FIG. 8, at 802, a linear cost component function may be used for a range of glucose values for the user. As shown in the example of FIG. 6, a linear cost function is used for glucose concentration 602 values between the hypoglycemic threshold 620 of 70 mg/dL and the hyperglycemic threshold 624 of 180 mg/dL. This range includes portions 610 and 612 of the piecewise cost function curve 606. At 804, a quadratic glucose cost function is used outside of the range where the linear glucose cost function is used. In the example of FIG. 6, the quadratic glucose cost function is used for glucose concentration 602 values below the hypoglycemic threshold 620 of 70 mg/dL and above the hyperglycemic threshold 624 of 180 mg/dL. Other ranges may be used with the respective cost function. As was discussed above relative to FIG. 6, this approach increases aggressiveness where needed and reduces aggressiveness where needed. This piecewise approach helps to reduce the persistent positive low level glucose excursions.

Figure 9:
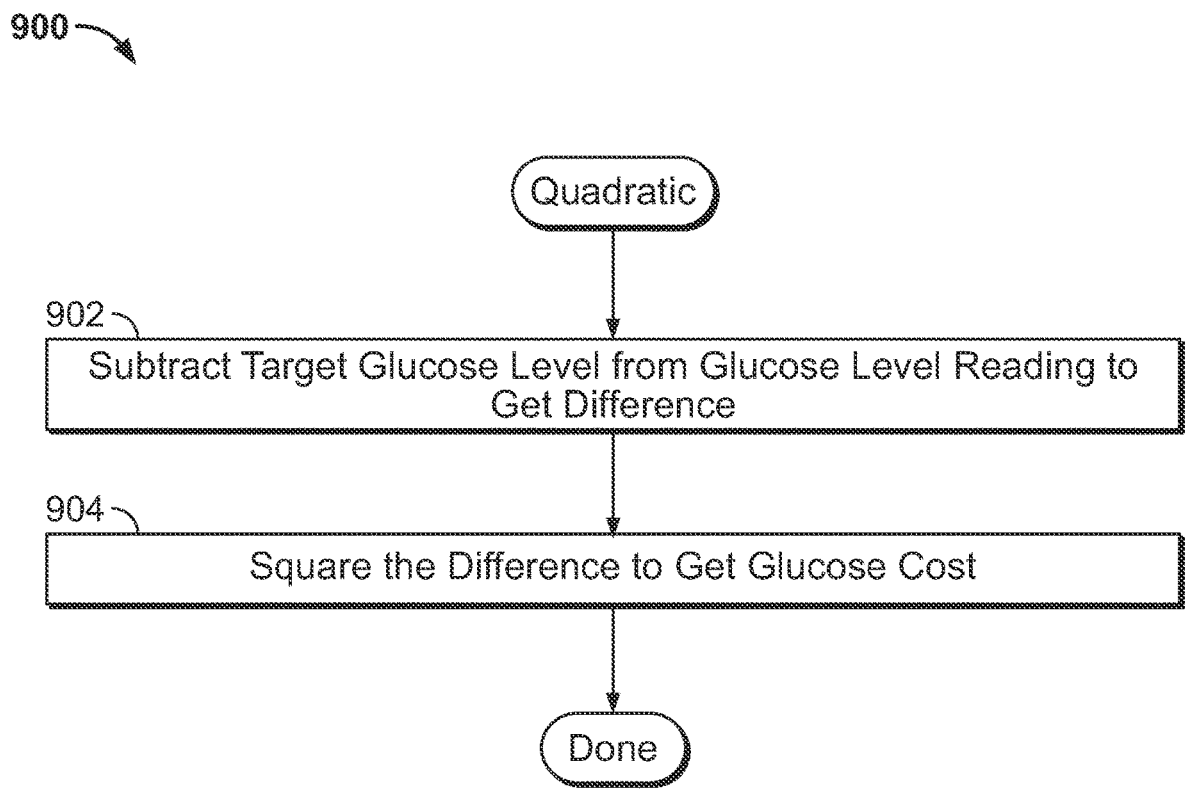
FIG. 9 depicts a flowchart of illustrative steps that may be performed in exemplary embodiments to calculate a quadratic glucose cost function value.

A suitable quadratic glucose cost function is:

$$J_{quad}(i)=(G(i)-SP(i))^2 \qquad \text{(Equation 1)}$$

where G(i) is the glucose level of the user at cycle i, and SP(i) is the target glucose level (e.g., concentration) for the user. FIG. 9 depicts a flowchart 900 of illustrative steps that may be performed in exemplary embodiments to determine a glucose cost using Equation 1 for a cycle i. At 902, the target glucose level (i.e., SP(i)) is subtracted from the glucose level at cycle i (i.e., G(i)). At 904, the resulting difference is squared. Thus, the glucose cost is the square of the difference between the user's current glucose value and the target glucose value.

A suitable linear glucose cost function to be used in the exemplary embodiments in a piecewise glucose cost function is:

$$J_{linear}(i)=(SP(i)-70)\cdot|G_{<SP(i)}(i)-SP(i)|+(180-SP(i))|G_{\geq SP(i)}(i)-SP(i)| \qquad \text{(Equation 2)}.$$

Figure 10:
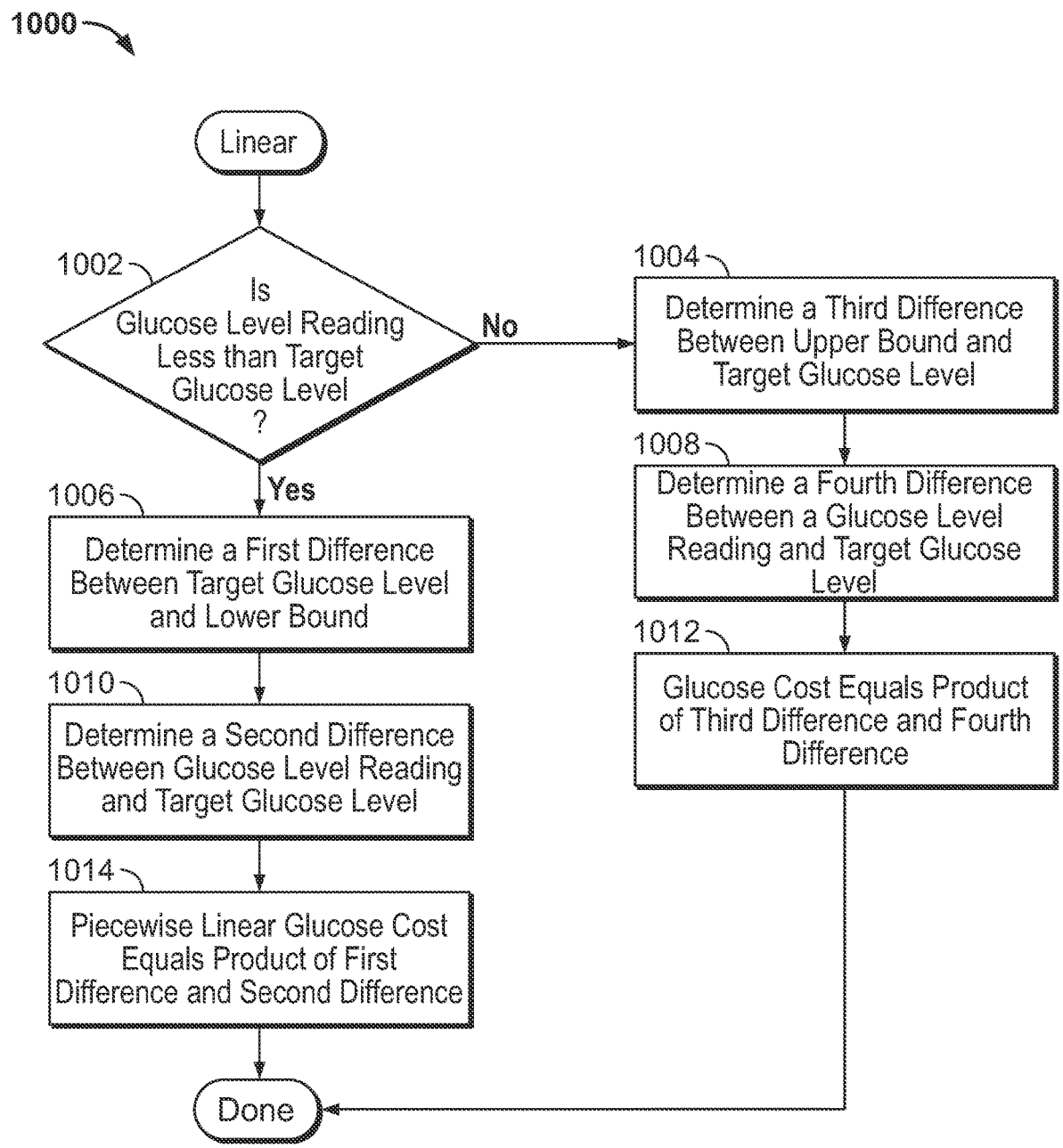
FIG. 10 depicts a flowchart of illustrative steps that may be performed in exemplary embodiments to calculate a linear glucose cost function value.

FIG. 10 depicts a flowchart 1000 of illustrative steps that may be performed to determine the linear glucose cost at cycle i using Equation 2. At 1002, a check is made whether the glucose level of the user G(i) is less than the target glucose level SP(i). If it is, at 1006, a first difference between the target glucose level and the lower bound (i.e., the hypoglycemic threshold of 70 mg/dL) is determined (i.e., (SP(i)−70)). At 1010, a second difference between the glucose level reading and the target glucose level is determined (i.e., $G_{<SP(i)}$(i)−SP(i)). At 1014, the piecewise linear glucose cost (i.e., $J_{linear}$(i)) is calculated as the product of the first difference and the second difference. The other portion of Equation 2 (i.e., (180−SP(i))|$G_{\geq SP(i)}$(i)−SP(i)|) is 0 as the glucose level of the user is not greater than or equal to the target glucose level.

If at 1002, the glucose level reading is not less than the target glucose level, a third difference between an upper bound (i.e., the hyperglycemic threshold) and the target glucose level is determined (i.e., 180−SP(i)). A fourth difference between the current glucose level reading of the user and the target glucose level is determined (i.e., $G_{\geq SP(i)}$(i)−SP(i)). At 1012, the piecewise linear glucose cost is determined to be the produce of the third difference and the fourth difference (i.e., (180−SP(i))|$G_{\geq SP(i)}$(i)−SP(i)|).

The combined piecewise glucose cost function, which combines the linear glucose cost function and the quadratic glucose cost function, may be expressed as:

$$J_{piecewise}(i)=(SP(i)-70)\cdot|G_{70\leq G<SP(i)}(i)-SP(i)|+(180-SP(i))|G_{SP(i)\leq G\leq 180}(i)-SP(i)|+(G_{<70}(i)-SP(i))^2+(G_{>180}(i)-SP(i))^2 \qquad \text{(Equation 3)}.$$

It should be appreciated that other formulations of the cost functions may be used. For example different weights may be used and the ranges where the cost functions are applied may be different than the above examples.

Figure 11:
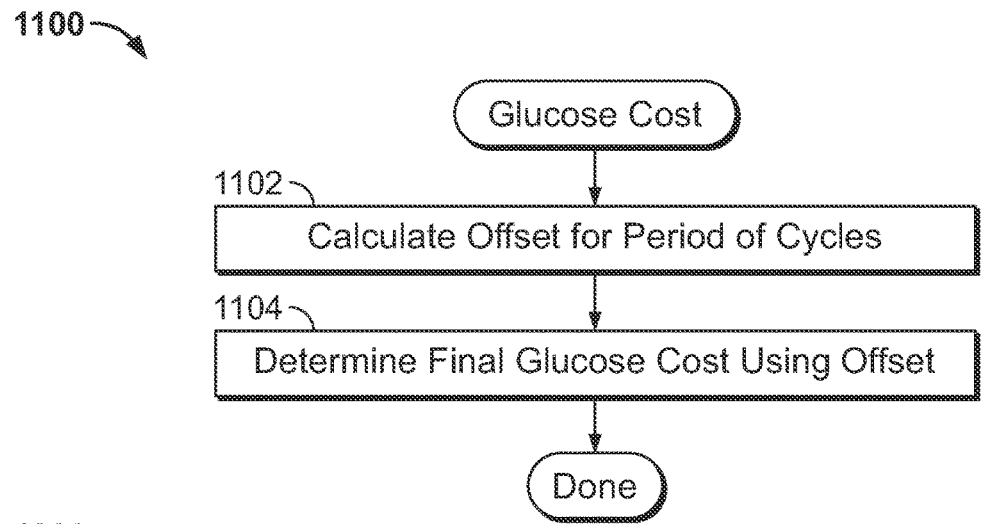
FIG. 11 depicts a flowchart of illustrative steps that may be performed in exemplary embodiments to calculate a final glucose cost function value.

As mentioned above, the glucose cost function may be further adjusted to attempt to better eliminate persistent positive low level glucose excursions. The use of the piecewise function $J_{piecewise}$(i) may be weighted based on how persistent the glucose excursions historically are and the magnitude of such persistent positive low level glucose excursions. In this regard, the exemplary embodiments may perform the illustrative steps depicted in the flowchart 1100 of FIG. 11. First, at 1102, an offset is calculated. The offset is a value between 0 and 1 that represents how often and how much the glucose level of the user exceeded the threshold over a recent period (that data of which may be found in the histories 111).

Figure 12:
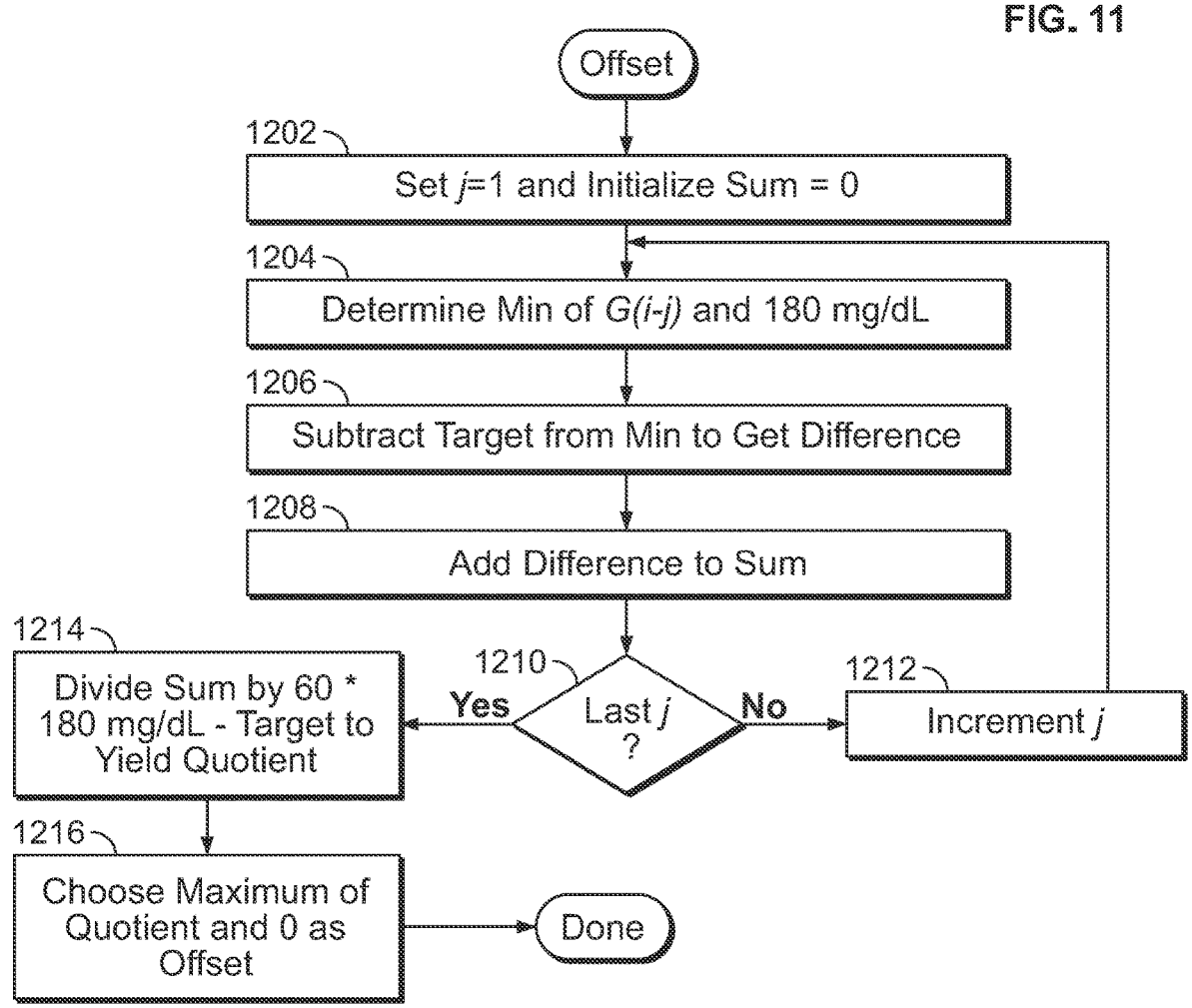
FIG. 12 depicts a flowchart of illustrative steps that may be performed in exemplary embodiments to calculate an offset value from historical glucose level data.
Figure 13:
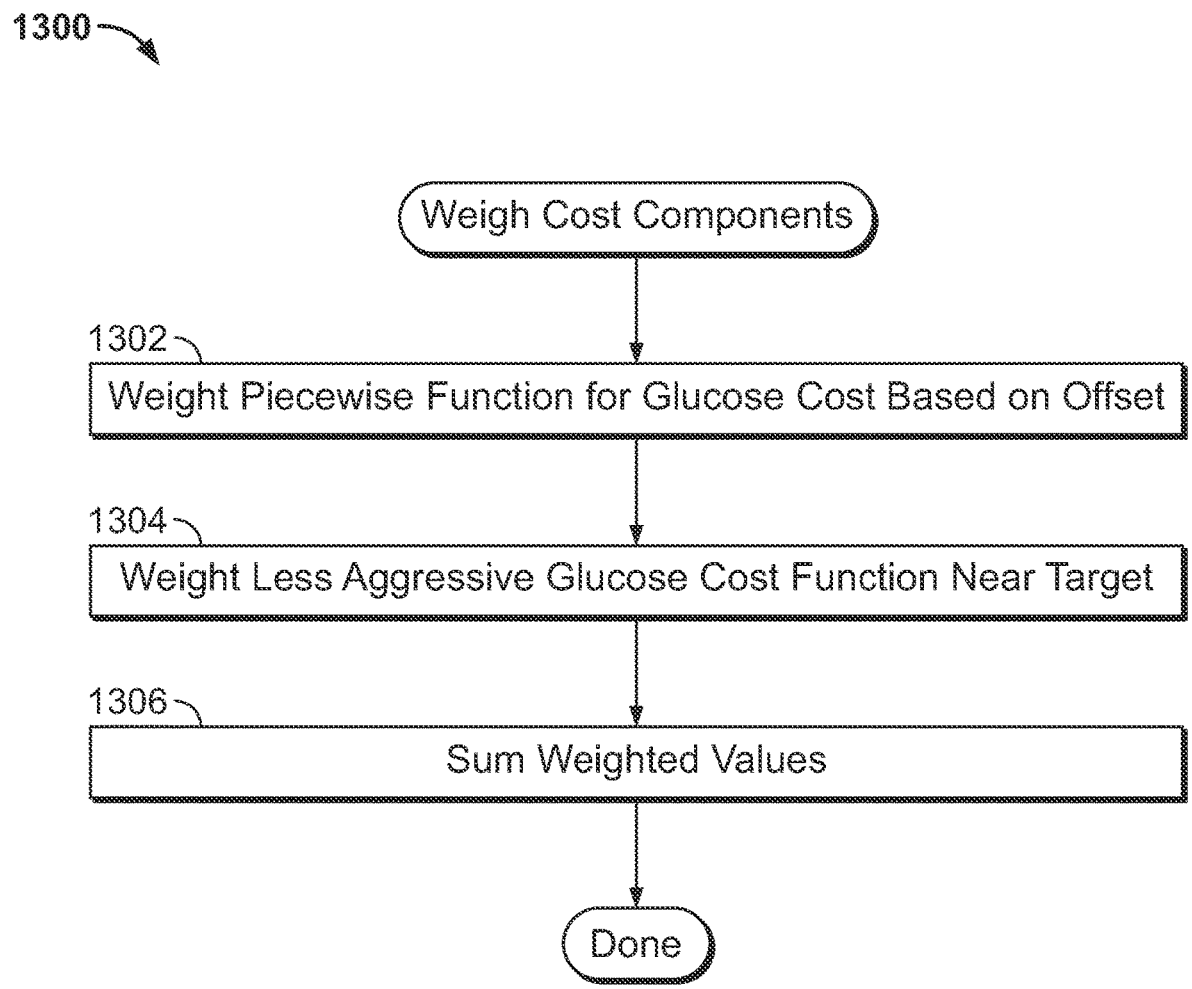
FIG. 13 depicts a flowchart of illustrative steps that may be performed in exemplary embodiments to weigh cost components in a final glucose cost function value.

One suitable formula for calculating the offset in exemplary embodiments is:

$$Q_{offset}(i) = \max\left(\frac{\sum_{j=1}^{60} \min(G(i-j), 180) - SP(i-j)}{60 \cdot (180 - SP(i-j))}, 0\right) \quad \text{(Equation 4)}$$

where max( ) is a function that returns a maximum of values and min( ) is a function that returns a minimum of values. FIG. 12 depicts a flowchart 1200 of illustrative steps that may be performed in exemplary embodiments to calculate the offset per Equation 4. At 1202, the variable j is initialized to have a value of 1 and $\Sigma_{j=1}^{60} \min(G(i-j),180)-SP(i-j)$ is initialized as 0. The index j is incremented from 1 to 60 in the summation as the period for which the values are aggregated is the 60 cycles prior to the current cycle i. Where each cycle is 5 minutes, the 60 cycles constitute a 5-hour period. Other lengths for the period may be used as well. At 1204, the minimum of G(i–j) and 180 is determined. This ensures that values greater than 180 are not selected. The value 180 constitutes the hyperglycemic threshold of 180 mg/dL. The units have not been explicitly recited in the equation. At 1206, a difference is calculated by subtracting the target glucose value from the minimum. At 1208, the difference is added to the aggregated sum. A check is made if j is the last j (e.g., 60). If not, at 1212, j is incremented and the process repeats beginning at 1204. The process repeats until all 60 cycles are processed. The resulting summation represents the aggregate sum of the differences with the maximum glucose value being 180.

When checked at 1210, if j=60, at 1214, the aggregate sum is divided by 60 times (180 mg/dL—the target glucose level). This produces a value indicative of the average amount that the glucose level of the user exceeds the target glucose level relative to the difference being (180 mg/dL—the target glucose level) each cycle of the period. At 1216, the maximum of the quotient calculated in 1214 and 0 is chosen as the quotient. Choosing the maximum eliminates negative values.

With reference to FIG. 11 again, once the offset has been calculated at 1102, the offset may be used to determine the final glucose cost. In one exemplary case, the final glucose cost may be calculated as:

$$J_{final}(i) = (1 - Q_{offset}(i)) \cdot J_{quad}(i) + Q_{offset}(i) \cdot J_{piecewise}(i) \quad \text{(Equation 5)}.$$

With this equation, the proportion of the final glucose cost function that utilizes the linear cost between 70-180 mg/dL versus the quadratic cost between 70-180 mg/dL can be determined based on the $Q_{offset}$ to allow the cost function to scale more rapidly with lower glucose excursions above the target glucose level. Specifically, the cost due to the linear cost function is more heavily weighted the higher the $Q_{offset}$, representing more persistent hyperglycemia.

FIG. 130 depicts a flowchart 1300 of illustrative steps that may be performed in exemplary embodiments to calculate the final glucose cost using the offset. At 1302, the weight applied to the piecewise function for glucose cost is determined. In Equation 5, the weight is the offset $Q_{offset}(i)$. At 1304, a weight is applied to the less aggressive glucose cost function near the target glucose value. In Equation 5, the quadratic glucose cost function is the less aggressive glucose cost function near the target glucose value. The weight in Equation 5 that is applied is $(1-Q_{offset}(i))$. At 1306, the weighted values are summed as in Equation 5.

While the application has described with reference to exemplary embodiments herein, it should be appreciated that various changes in form and detail relative to the exemplary embodiments may be made without departing from the intended scope as defined by the appended claims.

The invention claimed is:

1. A diabetic treatment medicament delivery device, comprising:
    a storage for storing medicament;
    a needle or cannula for delivery of the medicament to the user;
    a non-transitory storage medium for storing computer programming instructions for controlling operation of the diabetic treatment medicament delivery device;
    a processor for executing the computer programming instructions to cause the processor to:
        determine a selected basal diabetic treatment medicament dosage to be delivered by the diabetic treatment medicament delivery device to a user from among candidate basal diabetic treatment medicament dosages, the determining comprising determining the selected basal diabetic treatment medicament dosage based upon costs of the candidate basal diabetic treatment medicament dosages,
        wherein the cost is determined by a cost function for determining a cost for each of the candidate basal diabetic treatment medicament dosages, where, for each of the candidate basal diabetic treatment medicament dosages, the cost function includes a glucose cost component that punishes glucose excursions relative to a target glucose level that are anticipated to be experienced by the user if the candidate basal diabetic treatment medicament dosage is delivered to the user by the diabetic treatment medicament delivery device and a medicament cost component that punishes deviations between the candidate basal diabetic treatment medicament dosage and a basal delivery medicament dosage, and
        wherein the glucose cost component but not the medicament cost component varies in accordance with a first distribution function when the anticipated glucose excursions to be experienced by the user are in a first range and varies in accordance with a second distribution function when the anticipated glucose excursions to be experienced by the user are in a second range that differs from the first range; and
    cause the determined basal diabetic treatment medicament dosage to be delivered from the storage of the diabetic treatment medicament delivery device to the user via the needle or cannula.

2. The diabetic treatment medicament delivery device of claim 1, wherein the glucose cost component is a combination of a piecewise cost function and an additional cost function.

3. The diabetic medicament delivery device of claim 2, wherein weights assigned to the piecewise cost function and the additional cost function in the glucose cost component depend on persistence and magnitude of glucose excursions experienced by the user.

4. The diabetic treatment medicament delivery device of claim 1, wherein the first distribution function is a quadratic function.

5. The diabetic treatment medicament delivery device of claim 4, wherein the second distribution function is a linear function.

6. The diabetic treatment medicament delivery device of claim 1, wherein the second distribution function is a linear function.

7. The diabetic treatment medicament delivery device of claim 1, wherein the first distribution function is an exponential function or a logarithmic function.

8. The diabetic treatment medicament delivery device of claim 1, wherein the diabetic treatment medicament includes at least one of insulin, a glucagon-like peptide-1 (GLP-1) agonist, or pramlintide.

9. A medicament delivery device, comprising:
a storage for storing medicament;
a needle or cannula for delivery of the medicament to the user;
a non-transitory storage medium for storing computer programming instructions for controlling operation of the medicament delivery device;
a processor for executing the computer programming instructions as to cause the processor to:
determine a selected basal medicament dosage to be delivered by the medicament delivery device to a user from among candidate basal medicament dosages, the determining comprising determining the selected basal medicament dosage based upon costs of the candidate basal medicament dosages,
wherein the cost is determined by a cost function for determining a cost for each of the candidate basal medicament dosages, where, for each of the candidate basal medicament dosages, the cost function includes an analyte level component that punishes analyte level excursions relative to a target analyte level that are anticipated to be experienced by the user if the candidate basal medicament dosage is delivered to the user by the medicament delivery device and a medicament cost component that punishes deviations between the candidate medicament dosage and a basal delivery medicament dosage, and
wherein the analyte cost component varies in accordance with a first distribution function but not the medicament cost component when the anticipated analyte level excursions to be experienced by the user are in a first range and varies in accordance with a second distribution function when the anticipated analyte level excursions to be experienced by the user are in a second range that differs from the first range; and
cause the determined basal medicament dosage to be delivered from the storage of the medicament delivery device to the user via a needle or cannula.

10. The medicament delivery device of claim 9, wherein the analyte cost component is a combination of a piecewise cost function and an additional cost function.

11. The medicament delivery device of claim 10, wherein weights assigned to the piecewise cost function and the additional cost function in the analyte level cost component depend on persistence and magnitude of analyte excursions experienced by the user.

12. The medicament delivery device of claim 9, wherein the first distribution function is one of a quadratic function, an exponential function, a linear function or a logarithmic function.

13. A method performed by a processor of a medicament delivery device for controlling basal medicament deliveries by the medicament delivery device, comprising:
with the processor of the medicament delivery device, determining a medicament cost for a candidate basal medicament dosage for delivery to a user by the medicament delivery device;
with the processor, determining an analyte level cost for the candidate basal medicament dosage, the analyte level cost comprising:
where an analyte level of the user in a prediction horizon if the candidate basal medicament dosage is delivered to the user is within a specified range of a target analyte level of the user, a value produced by a linear function of a deviation between the analyte level of the user in the prediction horizon and the target analyte level of the user, and
where a analyte level of the user in the prediction horizon if the candidate basal medicament dosage is delivered to the user is outside a specified range of a target analyte level of the user, a value produced by a quadratic function of a deviation between the analyte level in the prediction horizon and the target analyte level of the user;
with the processor, determining a cost for the candidate basal medicament dosage using the medicament cost and the analyte level cost;
with the processor, based on the cost, deciding to deliver the candidate basal medicament dosage.

14. The method of claim 13, wherein the medicament is insulin.

15. The method of claim 13, further comprising weighting the analyte cost in the determining of the cost for the candidate basal medicament dosage.

16. The method of claim 15, further comprising weighting the medicament cost in the determining of the cost for the candidate basal medicament dosage.

17. The method of claim 15, wherein the cost for the candidate basal medicament dosage is the sum of the weighted medicament cost and the weighted analyte cost.

* * * * *